US00PP25797P2

(12) United States Plant Patent
Pounders et al.

(10) Patent No.: US PP25,797 P2
(45) Date of Patent: Aug. 11, 2015

(54) AZALEA PLANT NAMED 'AZ 35'

(50) Latin Name: *Rhododendron hybrida*
Varietal Denomination: AZ 35

(71) Applicants: The United States of America, as represented by the Secretary of Agriculture, A Government Agency, Washington, DC (US); Capstone Plants Inc., Grand Saline, TX (US)

(72) Inventors: Cecil T Pounders, Poplarville, MS (US); James B Berry, Mineola, TX (US)

(73) Assignees: CAPSTONE PLANTS, INC, Grand Saline, TX (US), part interest; THE UNITED STATES OF AMERICA AS REPRESENTED BY THE SECRETARY OF AGRICULTURE, Washington, DC (US), part interest ( * ) Notice: Subject to any disclaimer, the term of this patent is extended or adjusted under 35 U.S.C. 154(b) by 85 days.

(21) Appl. No.: 13/998,939

(22) Filed: Dec. 23, 2013

(51) Int. Cl.
*A01H 5/00* (2006.01)

(52) U.S. Cl.
USPC ..... Plt./239

(58) Field of Classification Search
USPC ..... Plt./239
See application file for complete search history.

*Primary Examiner* — Annette Para
(74) *Attorney, Agent, or Firm* — Penny J. Aguirre

(57) ABSTRACT

A new cultivar of Azalea named 'AZ 35' that is characterized by its compact, rounded plant habit with a top to bottom leaf canopy, its two distinct blooming periods from late March to early April and from late July into September in Texas and Mississippi, its spider form petals, that are pink in color and elongated in the spring and less elongated and tinted lavender in the fall, its narrow, sandpaper-textured foliage that is light green in color and blushed purple in the winter, its high level of resistance to spider mites, aphids, lace bugs, its high tolerance to heat stress, its stem and flower buds that are resistant to cold damage down to 14° F., its ease and speed of propagation by cuttings, and its very vigorous growth rate.

2 Drawing Sheets

Botanical classification: *Rhododendron hybrida.*
Cultivar designation: 'AZ 35'.

BACKGROUND OF THE INVENTION

The present invention relates to a new and distinct cultivar of *Rhododendron* plant of hybrid origin, botanically known as *Rhododendron hybrida* 'AZ 35' and will be referred to hereafter by its cultivar name, 'AZ 35'. 'AZ 35' is a new cultivar of evergreen Azalea grown for use as a landscape plant.

The new cultivar was developed through an on-going breeding program conducted by the Inventors in Poplarville, Miss. The objectives of the breeding program are to develop new cultivars of Azalea that exhibit tolerance to environmental stresses and disease resistance combined with unique flower colors and extended bloom periods.

The new cultivar arose from a cross made in spring 2005 using 'Primitive Beauty' (not patented) as the female parent and 'Fourth of July' (not patented) as the male parent. The Inventors selected 'AZ 35' as a single unique plant amongst the seedlings that resulted from the above cross in fall of 2007.

Asexual propagation of the new cultivar was first accomplished by softwood stem cuttings in Poplarville, Miss. in spring 2008 by one of the Inventors. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'AZ 35'. These attributes in combination distinguish 'AZ 35' as a new and distinct cultivar of Azalea.

1. 'AZ 35' exhibits a compact, rounded mound plant habit with a leaf canopy from top to bottom.
2. 'AZ 35' exhibits two distinct, strong blooming periods; blooming in the spring from late March to early April followed by a second bloom period in the fall from late July into September in Texas.
3. 'AZ 35' exhibits flowers with strap or spider form petals.
4. 'AZ 35' exhibits spring flowers that are pink in color with elongated petals and fall flowers that are tinted with lavender with less elongated petals.
5. 'AZ 35' exhibits mature foliage that is light green in color with a purple blush in the winter, narrow in shape, and sandpaper-like in texture.
6. 'AZ 35' exhibits a high level of resistance to spider mites, aphids, lace bugs.
7. 'AZ 35' exhibits a high tolerance to heat stress; thriving in summer temperatures that exceed 100° F. for 90 days or more.
8. 'AZ 35' exhibits stem and flower buds that are resistant to cold damage when exposed to temperatures down to 14° F.
9. 'AZ 35' produces many cuttings that are fast and easy to propagate.
10. 'AZ 35' exhibits a very vigorous growth rate.

The female parent of 'AZ 35', 'Primitive Beauty', differs from 'AZ 35' in having white flowers with only a spring bloom cycle and being less robust in plant vigor. The male parent, 'Fourth of July', differs from 'AZ 35' in having a weaker root system, in being less cold hardy, in having a later starting bloom period, in having a less rounded plant habit and being more difficult to propagate. 'AZ 35' can also be most closely compared to the *Rhododendron macrosepalum lin-*

*earifolium* (not patented) and the *Rhododendron* hybrid cultivar 'Koromo Shikibu' (not patented). *Rhododendron macrosepalum linearifolium* differs from 'AZ 35' in having flowers that are a different shade of pink with more narrow petals, having only one late spring bloom cycle, and having a weaker root system that is less tolerant of overwatering. Both *R. macrosepalum linearifolium* and 'Koromo Shikibu' are similar to 'AZ35' in having spider-form flowers as compare to the wider petals common to most cultivated azalea clones. 'Koromo Shikibu' differs from 'AZ 35' in having flowers that are lavender in color, in having one bloom period, and in having a more robust open growth habit.

BRIEF DESCRIPTION OF THE DRAWINGS

The accompanying colored photographs illustrate the overall appearance and distinct characteristics of the new Azalea. The photographs were taken of six year-old plants of 'AZ 35' as grown outdoors in a 20-gallon container in Poplarville, Miss.

The photograph in FIG. 1 provides a close-up view of the spring flowers of 'AZ 35'.

Figure 1:
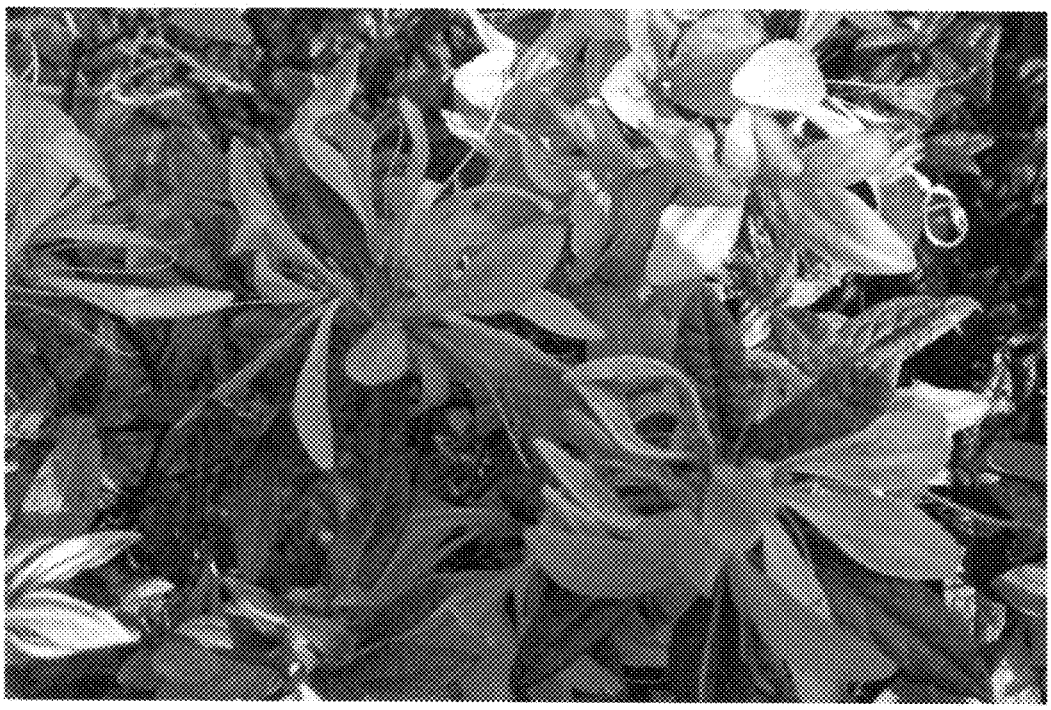
Figure 2:
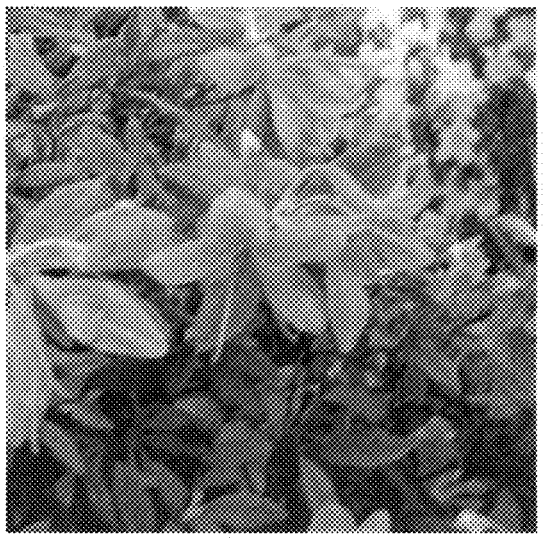

The photograph in FIG. 2 provides a close-up view of the fall flowers of 'AZ 35'.

Figure 3:
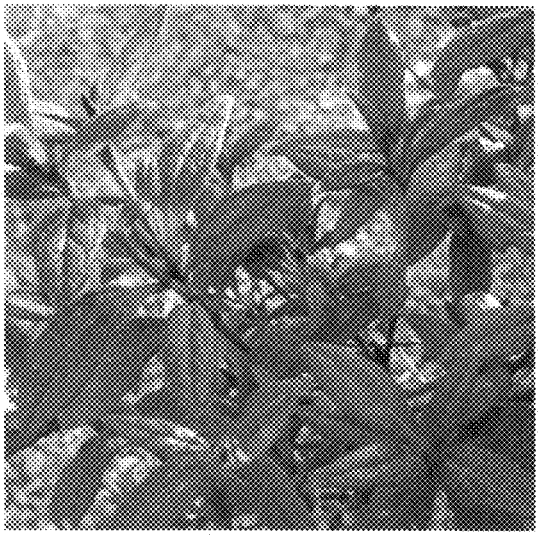

The photograph in FIG. 3 provides a close-up view of the winter foliage of 'AZ 35'.

Figure 4:
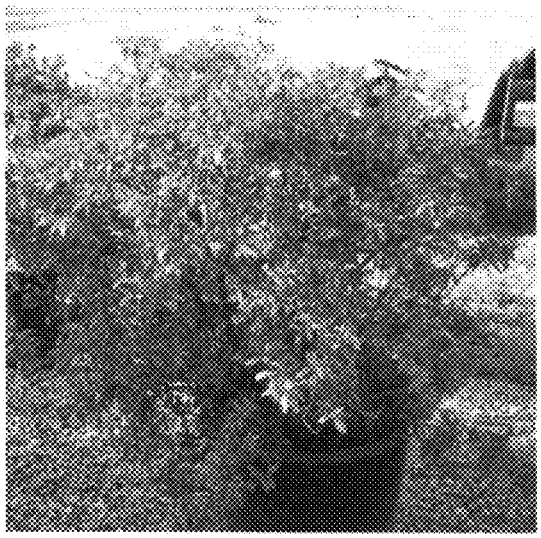

The photograph in FIG. 4 provides an overall view of the plant habit of 'AZ 35'.

The colors in the photographs are as close as possible with the digital photography and printing techniques utilized and the color codes in the detailed botanical description accurately describe the new Azalea.

DETAILED BOTANICAL DESCRIPTION OF THE PLANT

The following is a detailed description of two year-old plants of the new cultivar as grown outdoors in 3-gallon containers in a greenhouse in Grand Saline, Tex. with mature size described for plants 6 years in age as grown outdoors in a trial bed under overhead irrigation in Poplarville, Miss. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Late March to early April and late July to September in Texas.

*Plant type*.—Evergreen shrub.

*Plant habit*.—Upright, rounded, and compact with a leaf canopy from top to bottom.

*Height and spread*.—Reaches up to 1.3 m in height and 1.5 m in spread as grown for 6 years.

*Hardiness*.—At least in U.S.D.A. Zones 7 and 8, exhibits a high tolerance to heat stress; thriving in summer temperatures that exceed 100° F. for 90 days or more with stem and flower buds that are resistant to cold damage when exposed to temperatures down to 14° F.

*Diseases*.—High level of resistance to mites, aphids, lace bugs.

*Root description*.—Abundant and fibrous.

*Propagation*.—Softwood cuttings, readily propagated.

*Growth rate*.—Very vigorous.

Stem description:

*Shape*.—Round.

*Stem color*.—New growth; 138D suffused with 185A, mature wood; 165A.

*Stem size*.—Main stems; 1, an average of 7 cm in length and 1 cm in width, lateral stems; an average of 22 cm in length and 3 mm in diameter.

*Stem surface*.—New growth; sparsely covered with woolly hairs, 1 mm in length and 22A, mature wood; ridged bark, exfoliating.

*Stem aspect*.—Held upright at an average angle of 15° (0°=vertical).

*Stem strength*.—Strong.

*Branching*.—Densely-branched, an average of 50 lateral branches in a 3-gallon container.

*Internode*.—Average of 1.5 cm in mid-range of lateral branches.

Foliage description:

*Leaf shape*.—Lanceolate.

*Leaf division*.—Simple.

*Leaf base*.—Cuneate.

*Leaf apex*.—Acuminate.

*Leaf venation*.—Pinnate, upper and lower surface; 145C in color, both surfaces moderately covered with woolly pubescence, upper surface; color matches leaf color, 1 mm in length, lower surface; 26A in color and 1 mm in length.

*Leaf margins*.—Entire and lightly pubescent.

*Leaf attachment*.—Petiolate.

*Leaf arrangement*.—Alternate.

*Leaf orientation*.—Held horizontal to upright.

*Leaf aspect*.—Upright and slightly cupped downward.

*Leaf surface*.—Upper and lower surface, coriaceous, cartilaginous (sandpaper-like), and shiny.

*Leaf color*.—Young leaves upper and lower surface; 144A, mature leaves upper surface; 146A, blushed with 94A to 94C in the winter, mature leaves lower surface; 146C.

*Leaf size*.—Average of 4 cm in length, and 1.5 cm in width.

*Leaf quantity*.—About 25 leaves per lateral branch 22 cm in length.

*Petioles*.—Average of 4 mm in length and 1 mm in diameter, 151C in color, thickly covered with long woolly hairs 170C in color and 2 mm in length.

Flower description:

*Inflorescence type*.—Flowers are solitary and occasionally in pairs.

*Lastingness of flowers*.—About 10 days, self cleaning.

*Flower size*.—An average of 5 cm in depth and 4 cm in diameter.

*Flower fragrance*.—None.

*Flower shape*.—Spider form with flared petal lobes.

*Flower number*.—Average of 4 per lateral stem.

*Flower aspect*.—Upright.

*Flower bud*.—Lanceolate to ovate in shape, an average of 2 cm in length and 7 mm in diameter, acute apex, color; N78A and 83B.

*Flower attachment*.—Pedicel.

*Petal number*.—5.

*Petal shape*.—Spatulate (strap-like) with upper portion oblanceolate, in the fall the petals are less elongated with the upper portion elliptic.

*Petal aspect*.—About 10% fused into tube with lobes flared outward and slightly overlapping.

*Petal color*.—Spring; N74A to N74C with base 70C and internal freckles 72A, fall; a blend between N74C and 75A.
*Petal surface*.—Both surfaces glabrous.
*Petal margins*.—Entire and slightly wavy.
*Petal apex*.—Rounded.
*Petal base*.—Fused.
*Petal size*.—Average of 3.5 cm in length and 1.3 cm in width.
*Petaloids*.—None.
*Sepal number*.—5.
*Sepal shape*.—Lanceolate arranged in a whorl.
*Sepal margin*.—Entire.
*Sepal size*.—Average of 5 mm in length and 3 mm in width.
*Sepal aspect*.—Upright.
*Sepal surface*.—Outer surface; dull, slightly sticky to the touch and densely covered with long soft pubescence up to 3 mm in length and NN155A in color, inner surface smooth and dull.
*Sepal apex*.—Acute-slightly acuminate.
*Sepal base*.—Fused.
*Sepal color*.—Outer and inner surface; 144B with very light striping of 187B.
*Calyx*.—Campanulate in shape, average of 6 mm in length and 5 mm in diameter.
*Peduncles*.—An average of 1.3 cm in length and 1 mm in diameter, surface is slightly glossy and densely covered with soft pubescence up to 2 mm in length and NN155A in color, color; base is 144C, then blends to 185A at mid-section to apex.
*Pedicels*.—An average of 1.4 cm in length and 2 mm in diameter, flexible strength, held upright, pubescent surface, N74A in color.
*Bracts*.—Average of 3 at base of flower or pair, wedge-shaped and cupped inward and occasionally with leaf-like tip, about 8 mm in length and 5 mm in width, base cuneate, apex acute, outer surface glabrous, sticky to the touch and covered densely with pubescence 2 mm in length and 163A in color, inner surface very glossy and smooth, color: outer and inner surfaces; base 145C, mid-section 144C and apex 144B.

Reproductive organs:

*Gynoecium*.—1 Pistil, stigma; club-shaped, about 1 mm in diameter and a color between 60A and N74A, style; 3.5 cm in length, 0.5 mm in width and 63A in color, ovary; conical in shape, 4 mm in length and 3 mm in width, 152A in color.
*Androecium*.—Stamens; average of 5, filament; average of 2.2 cm in length, N74A in color, anthers; not distinct, few in number and 72A in color; no pollen observed.
*Fruit/seeds*.—Young seed pod; 1 cm in length, 3 mm in width, inside the seed pod are many fine string like hairs up to 9 mm in length and NN155A in color, inside and outside are glossy, color is N144A and N144C at the tip, mature seed pod; an average of 1 cm in length and 5 mm in width, surfaces inside and outside are slightly glossy and slightly sticky to the touch, inside the seed pod are fine string like hairs up to 2 cm in length and NN155A in color, inside and outside color is a blend between 145A and 138C suffused with a blend between 183A and 200A.

It is claimed:

1. A new and distinct cultivar of Azalea plant named 'AZ 35' as herein illustrated and described.

* * * * *